United States Patent
Odame et al.

(10) Patent No.: US 12,419,537 B2
(45) Date of Patent: Sep. 23, 2025

(54) DEVICE FOR AUTOMATICALLY DETECTING LUNG FUNCTION VARIABILITY

(71) Applicant: THE TRUSTEES OF DARTMOUTH COLLEGE, Hanover, NH (US)

(72) Inventors: Kofi Odame, Hanover, NH (US); Justice Amoh, Hanover, NH (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 769 days.

(21) Appl. No.: 17/264,949

(22) PCT Filed: Jul. 31, 2019

(86) PCT No.: PCT/US2019/044299
§ 371 (c)(1),
(2) Date: Feb. 1, 2021

(87) PCT Pub. No.: WO2020/028470
PCT Pub. Date: Feb. 6, 2020

(65) Prior Publication Data
US 2021/0315480 A1    Oct. 14, 2021

Related U.S. Application Data

(60) Provisional application No. 62/712,262, filed on Jul. 31, 2018.

(51) Int. Cl.
*A61B 5/08* (2006.01)
*A61B 5/00* (2006.01)
(Continued)

(52) U.S. Cl.
CPC .......... *A61B 5/0816* (2013.01); *A61B 5/0823* (2013.01); *A61B 5/1135* (2013.01);
(Continued)

(58) Field of Classification Search
CPC ............... A61B 5/0816; A61B 5/0823; A61B 5/1135; A61B 5/14542; A61B 5/6823;
(Continued)

(56) References Cited

U.S. PATENT DOCUMENTS

| 2004/0087839 | A1 | 5/2004 | Raymond et al. |
| 2012/0041279 | A1* | 2/2012 | Freeman ............... A61B 5/0803 600/534 |
| 2013/0060150 | A1* | 3/2013 | Song ...................... A61B 7/003 600/529 |

(Continued)

OTHER PUBLICATIONS

Che, Zhengping et al. "Recurrent Neural Networks for Multivariate Time Series with Missing Values", Apr. 17, 2018, Nature Scientific Reports, (2018) 8:6085, pp. 1-12. (Year: 2018).*

(Continued)

*Primary Examiner* — Tse W Chen
*Assistant Examiner* — Evelyn Grace Park
(74) *Attorney, Agent, or Firm* — Cozen O'Connor

(57) ABSTRACT

A device for detecting and quantifying lung function includes a piezoelectric sensor configured for attachment to a mammalian chest wall and to feed signals to an ADC providing digitized signals to a processor. The processor firmware extracts inspiration and expiration times from the digitized signals and generates an I/E ratio from them. The processor has firmware to detect wheezing sounds in the signals. The device has an analog event detector configured to wake-up the processor upon detection of candidate wheeze sounds in the signals. In embodiments, the analog event detector includes bandpass filters coupled to a modeling circuit feeding a correlation circuit, the filters having bandpass adjusted by feedback from a circuit within the analog event detector. In an embodiment, the device uses an FFT with a gated recurrent unit (GRU) with partial reset (GRUPR) neural network to detect wheezes.

20 Claims, 8 Drawing Sheets

(51) Int. Cl.
*A61B 5/113* (2006.01)
*A61B 5/145* (2006.01)

(52) U.S. Cl.
CPC ........ *A61B 5/14542* (2013.01); *A61B 5/6823* (2013.01); *A61B 5/7225* (2013.01); *A61B 5/7257* (2013.01); *A61B 5/7264* (2013.01)

(58) Field of Classification Search
CPC ................ A61B 5/7225; A61B 5/7257; A61B 5/7264; A61B 5/08–087; A61B 7/003; A61B 5/14551
See application file for complete search history.

(56) References Cited

U.S. PATENT DOCUMENTS

| | | | |
|---|---|---|---|
| 2013/0090567 A1* | 4/2013 | Lee | ........................ A61B 5/725 600/529 |
| 2015/0164375 A1 | 6/2015 | Schindhelm et al. | |
| 2015/0164433 A1 | 6/2015 | Halperin et al. | |
| 2018/0106897 A1* | 4/2018 | Shouldice | .............. G06V 40/00 |
| 2018/0177483 A1 | 6/2018 | Ye et al. | |
| 2019/0083001 A1 | 3/2019 | Stamatopoulos et al. | |

OTHER PUBLICATIONS

International Patent Application No. PCT/US2019/044299, International Search Report and Written Opinion dated Nov. 1, 2019, 14 pgs.

Sebastian et al. (Jul. 2018), "Tutorial: Brain-inspired computing using phase-change memory devices", J. Appl. Phys.

Lin et al. (Jan. 2014), "An FPGA-Based Rapid Wheezing Detection System", Int. J. Environ. Public Health 2014, 11, 1573-1593.

Oletic et al. (Apr. 2014), "Low-Power Wearable Respiratory Sound Sensing", Sensors 2014, 14, 6535-6566.

* cited by examiner

Time (s)

DEVICE FOR AUTOMATICALLY DETECTING LUNG FUNCTION VARIABILITY

CROSS-REFERENCE TO RELATED APPLICATIONS

Priority Claim

The present application is a 35 U.S.C. § 371 filing of International Application No. PCT/US2019/044299 filed Jul. 31, 2019, which claims priority to U.S. Provisional Patent Application No. 62/712,262 filed Jul. 31, 2018. The entire contents of the provisional application are incorporated herein by reference.

FIELD

The present application relates to the field of lung function monitoring devices, such as are useful in monitoring and treating asthma, chronic obstructive pulmonary disease (COPD), and other pulmonary disorders of humans and other mammals.

BACKGROUND

Classical lung function testing in humans and other mammals includes testing for forced vital capacity (FVC) and forced expiratory volume in one second (FEV1). FEV1 is of particular interest in monitoring COPD and asthma because restrictions in expiratory airflow caused by these conditions may make breathing difficult, cause audible wheezing, and produce other symptoms. FEV1 measurements of patients suffering from other diseases, such as pneumoconiosis or silicosis, or recovering from pneumonia, may also be useful to treating physicians.

Asthma signs and symptoms, including FEV1, often vary from day to day or from week to week because asthma symptoms may be triggered by environmental conditions including specific pollens, medications, or foods and breathing cold air as well as exercise and many common viruses and bacteria. Asthma is often treated with one or more medications including short-acting beta agonists and longer-acting "controller" medications such as antihistamines and systemic or inhaled steroids; patients having frequent variations in symptoms, including frequent asthma attacks, may need adjustment in their prescribed medications as well as identification and avoidance of specific environmental triggers. A 12% FEV1 change during a 2-week window is indicative of poor asthma control, which can lead to emergency room visits or hospitalization—detection of such a change is desirable so that the patient's drug protocol can be adjusted. For newly-diagnosed asthma patients, accurate monitoring may mean fewer, more efficient office visits needed to establish a treatment plan and achieve asthma control.

Lung transplants and other open-chest surgery typically leads to post-operative pain; post-operative pain and other issues may lead to impaired lung function. After lung transplantation, the patient's pulmonary function should eventually stabilize and vary by 5% or less; an FEV1 or FVC decline of 10% for more than 2 days is indicative of either rejection or infection of the transplanted lung. Whenever complications occur, a timely response is crucial for successful treatment.

Many acute respiratory illnesses, including recovery from pneumonia, are managed with bronchodilator therapy, which often is guided by evaluation of the patient's pulmonary function.

Daily monitoring of lung function can also be of use during clinical trials of new drugs, including drugs intended for treatment of COPD or asthma. Such monitoring can not only detect changes in symptoms that may be induced by study drugs, but may help verify adherence to study protocols.

SUMMARY

A device for detecting and quantifying lung function includes a piezoelectric sensor configured for attachment to a mammalian chest wall and to feed signals to an analog-to-digital converter (ADC) providing digitized signals to a processor. The processor firmware extracts inspiration and expiration times from the digitized signals and generates an I/E ratio from them. The processor has firmware to detect wheezing sounds in the signals. The device has an analog event detector configured to wake-up the processor upon detection of candidate wheeze sounds in the signals. In embodiments, the analog event detector includes bandpass filters coupled to a modeling circuit feeding a correlation circuit, the filters having bandpass adjusted by feedback from a circuit within the analog event detector. In an embodiment, the device uses a fast Fourier transform (FFT) with a gated recurrent unit (GRU) with partial reset (GRUPR) neural network to detect wheezes.

DETAILED DESCRIPTION OF THE EMBODIMENTS

Lung function, and variations in lung function, are important factors for determining a patient's level of asthma impairment. Specifically, a forced expiratory volume in one second (FEV1) change of 12% during a two-week window is indicative of poor asthma control. Since daily visits to the hospital for pulmonary function testing is impractical, it would be ideal to monitor lung function at home or while performing other activities of normal living. Unfortunately, current tools for monitoring lung function at home are highly unreliable; their dependence on patient adherence and technique often produces incorrect, incomplete, or even invented records.

The purpose of our invention is to passively monitor a patient's changes in FEV1/forced vital capacity (FEV1/FVC) outside of a hospital in settings such as at home, at work, while shopping, or while performing other activities of normal living.

For a single breathing cycle, the inspiration time (Ti) refers to the duration of inhalation, whereas the expiration time (Te) denotes the duration of exhalation. The time taken for a complete cycle of inhalation and exhalation is the total cycle time (Tt). Additional relevant respiratory timing parameters can be obtained as functions of these three:

$$\text{Respiratory Rate} = 60/Tt \text{ bpm};$$

$$I{:}E \text{ Ratio} = Ti/Te;$$

$$\text{Fractional Inspiratory Time} = Ti/Tt$$

Respiratory rate (RR) is the inverse of the cycle time, expressed in number of breaths per minute (bpm). Respiratory rate is a common vital sign that is monitored clinically to detect changes in patient physiology along with other signs like body temperature and heart rate. Healthy adults have RR values between 12-18 bpm, whereas those for children are higher between 17-30 bpm. Abnormally high rate of respiration is known as tachypnea and is indicative of increased work of breathing (WoB). Increased WoB during normal breathing occur when additional work is required for inhalation and exhalation because the airways are obstructed. Increased respiratory rate can therefore reveal airway obstruction.

Inspiratory-to-expiratory time ratio (I:E Ratio) is an important derived timing parameter. I:E Ratio has been shown to be a good indicator of respiratory dysfunction. For healthy normal breathing in adults, exhalation is expected to last for about twice as long as inhalation, resulting in an I:E ratio of 1:2. Inhalation is shorter because it is active and requires the use of accessory muscles. On the other hand, exhalation takes longer because it is more passive. However, when the airways are obstructed such as in asthma patients, expiration is further prolonged leading to decreased I:E ratios of 1:3 or 1:4. The last derivative respiratory timing parameter considered is the fractional inspiratory time (FIT). FIT is the respiratory "duty cycle" and is derived from I:E Ratio as:

$$1/FIT = 1 + 1/IER = (Ti + Te)/Ti = Tt/Ti$$

As in IER, low values of FIT could also detect airway obstruction.

Figure 1:
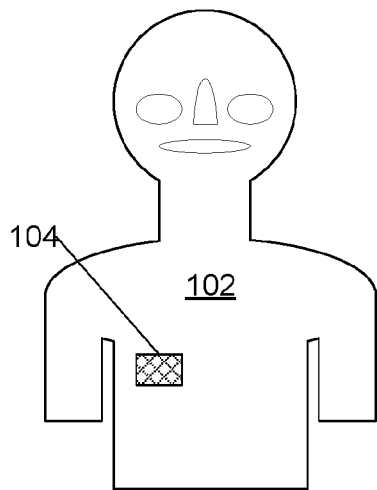
FIG. 1 illustrates placement of an embodiment of the lung function monitor on a patient.

The Passive Unobtrusive Lung Function Monitor 104 (PULMO) (FIG. 1) is our novel wearable device for unobtrusively detecting pulmonary function variability in the ward or at home. It is worn on the chest 102 of a subject while that subject remains outside of hospital settings, typically at home, at work, while shopping, and while performing other activities of normal daily living. It is part of a suite of respiratory disease monitoring tools, including inhaler use detection and cough frequency count detection devices, that may be used to monitor patients having respiratory diseases such as COPD, Asthma, cystic fibrosis, or pneumoconiosis, who are recovering from lung-related issues such as pneumonia, lung transplant, or surgery that required opening the chest, or who are participating in clinical trials of drugs intended for treatment of respiratory diseases or lung-related issues. PULMO automatically extracts FEV1/FVC pulmonary function information from passively-measured physiological signs, requiring no active engagement from the user or clinician, is in a light-weight "Band-Aid" form factor intended for sticking to a subject's chest, and has a 14-day battery life. PULMO requires no obtrusive changes to the user's daily routine.

Each PULMO device 200 (FIG. 2) includes a piezoelectric sensor 202, in a particular embodiment the piezoelectric sensor 202 is a contact microphone having a sensing plate formed of lead zirconium titanate (PZT) with deposited electrodes and, when the PULMO device is attached to a subject's 102 chest, is configured to sense strain and vibration of the subject's chest at frequencies ranging from less than ten hertz to at least one kilohertz. A particular embodiment has dimensions W×H×L=2×5×1 cm, with weight 10 grams, although other embodiments have different physical sizes and shapes.

The piezoelectric sensor 202 of the PULMO device feeds through a 14-bit ADC 204 at a sampling rate of about 10 kilosamples per second into a low-power ARM-based microcontroller 206 operating under control of firmware 210 in memory 208. Sensor 202 is sensitive to sounds in the range 10-80 dB SPL, including heart (20-100 Hz band) and faint lung sounds (70 Hz-1 kHz band) that have traveled through the parenchyma and to the soft tissue region, as well as low frequency (10 Hz and less) chest respiratory movements. The device also incorporates accelerometers 220 coupled to the ADC 204 such that motion-related signals can be read by the processor or microcontroller 206. The device is adapted to the wide range of signal levels encountered with different sensor placements and different body mass indexes across subjects. The microcontroller 206 is adapted to record data into an electrically erasable and programmable read-only memory (EEPROM) 212, which in a particular embodiment is a micro SD card, and in a particular embodiment is adapted to transmit data over a short-range digital radio 214. The PULMO device is adapted to be powered by a battery 216 that may, in some embodiments, be charged through an integral wireless charger 218. An analog event detector 205 is coupled to receive signals from sensor 202, to determine when events of interest, such as wheezes, may be occurring, and to wake up processor 206 upon detection of these candidate events such the processor may record sounds and process them to analyze the events of interest and determine if sounds present in analog signals received by the piezoelectric sensor 202 represent actual wheezes or other significant events. In embodiments, a clock-timer 222 is included so that time of events may be recorded with data representing recorded events. Recorded events may include detected wheezes and episodes of significantly reduced FEV1/FVC.

In some embodiments, the PULMO device includes a photoplethysmographic sensor 230, sometimes known as a pulse oximeter sensor, adapted to detect pulse rate and oxygen saturation in skin underlying the PULMO device. In order to conserve power, the photoplethysmographic sensor operates under command of processor 206 to measure oxygen saturation, and in some embodiments pulse rate, when the processor has been awakened and needs measured oxygen saturation to evaluate a wheezing event, coughing event, and/or determine FEV1/FVC ratios.

The firmware 210 includes machine readable instructions adapted to analyze measured sounds, as received by the piezoelectric sensor 202, to detect cough, inhaler use and wheezing. In addition, the firmware 210 includes machine readable instructions adapted to determine FEV1/FVC from measured physiological signals including measured sounds, and, in embodiments having photoplethysmographic sensor 230, measured pulse rate and blood oxygen saturation. An accelerometer 220 is used to detect nighttime awakenings and changes in activity, using standard activity detection methods.

In an embodiment, the inspiratory/expiratory (IE) ratio is determined from breathing-related expansion and contraction of the chest wall.

Figure 4:
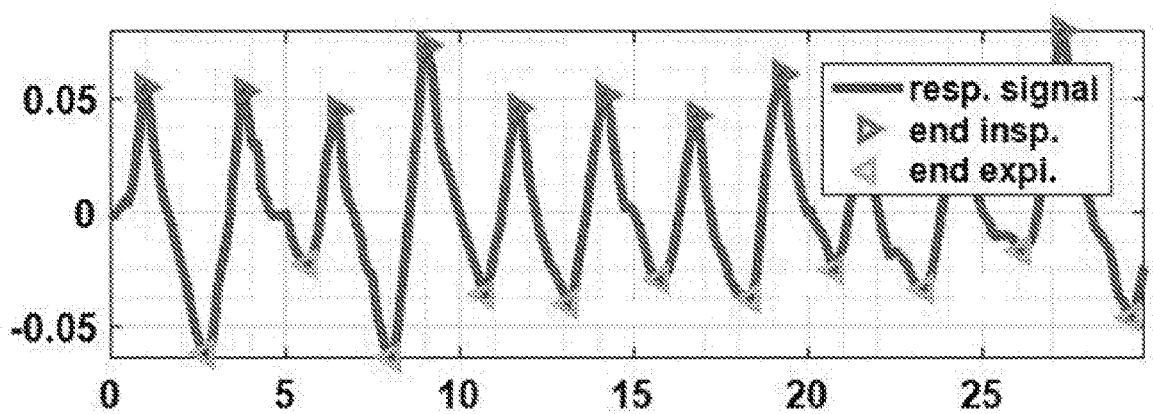
FIG. 4 is a graph that represents strain induced by a subject's respirations as detected by the piezoelectric transducer.

In an embodiment, inspiration Ti and expiration Te times, as well as total respiration cycle time Tt, are extracted from recorded strain as recorded by the piezoelectric sensor and illustrated in FIG. 4. These times are used to directly calculate I:E ratio using the equations given above. This ratio is then processed to estimate FEV1/FVC ratio. In embodiments, a multi-variable regression model is used to determine FEV1/FVC from the respiratory rate, I:E ratio, pulse or heart rate, as well as known race, age and height of the wearing patient.

Figure 3:
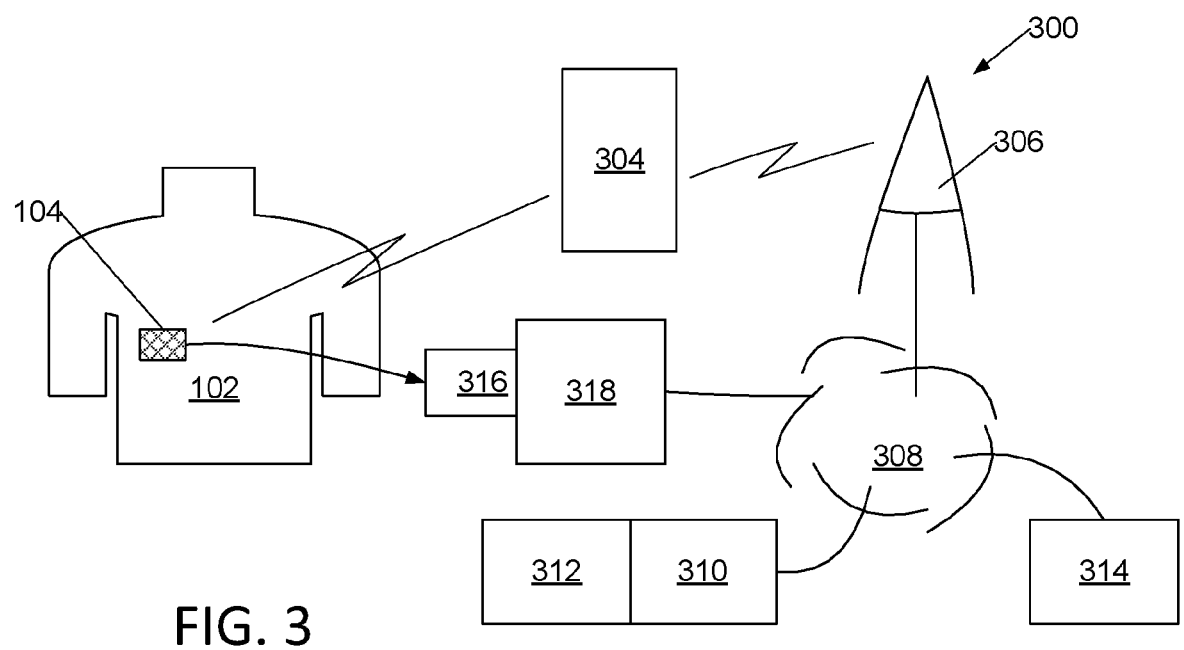
FIG. 3 is a block diagram of a system including a body area network (BAN) incorporating an embodiment of the lung function monitor.

A system 300 (FIG. 3) incorporating the PULMO monitor 104, 200, records sounds and motions of the subject's chest 102 and processes this data into data recorded in EEPROM memory 212. In embodiments incorporating digital radio 214, this recorded data may be transferred by radio to a cell phone 304, where it may be further sent by the cell phone 304 to a local cell tower 306 and thence over internet 308 to a server 310 where it is recorded in a database 312 and made available to a physician (not shown) at a workstation 314. In embodiments, including embodiments lacking digital radio 214, the EEPROM memory 212, 316 may be removed and inserted into a workstation 318, whereupon the data may be transferred over internet 308 to server 310 and database 312.

Figure 5:
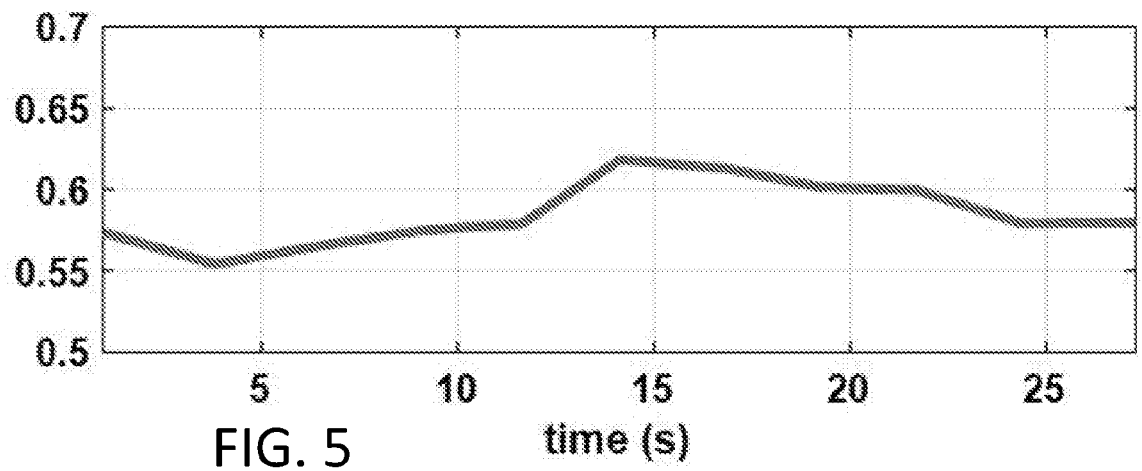
FIG. 5 is a graph that represents inspiration and expiration volume ratios as extracted from the strain illustrated in FIG. 4.
Figure 6:
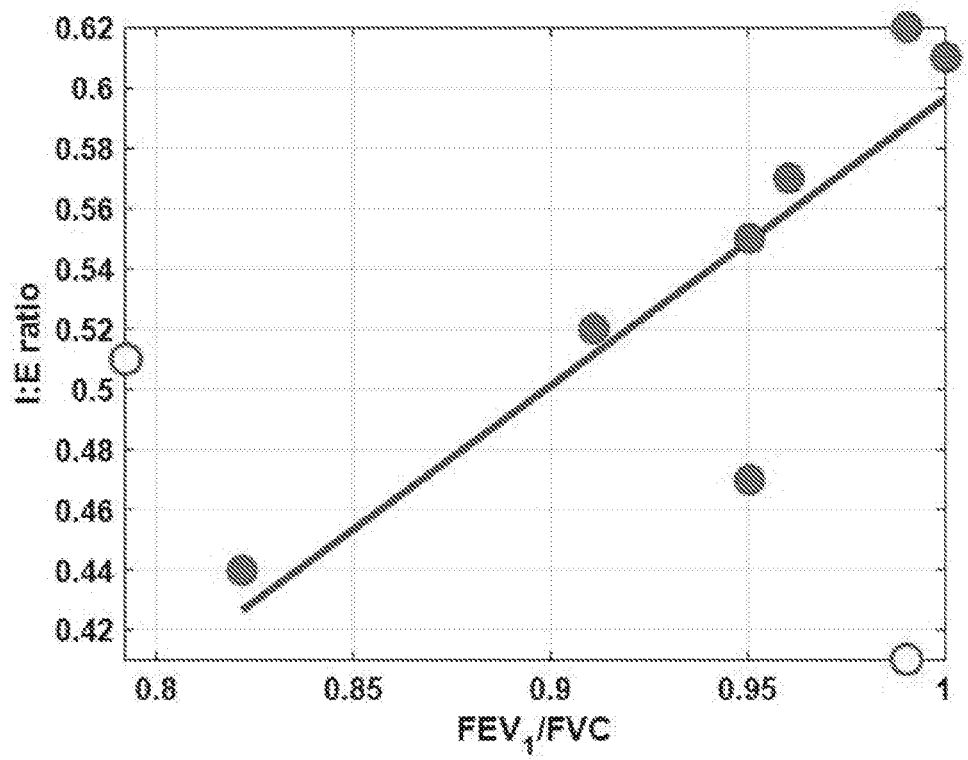
FIG. 6 illustrates correlation between inspiration/expiration ratio and FEV1/FVC ratios.

As the subject's chest moves with inspiration and expiration, it produces strain that can be sensed by the piezoelectric sensor 202, producing a signal illustrated in FIG. 4. From this signal, an inspiratory:expiratory (I:E) ratio can be extracted by processor 206, as shown in FIG. 5. The I:E ratio correlates with an FEV1/FVC, as illustrated in FIG. 6.

The PULMO monitor also passively measures additional physiological signals including heart rate from received sound signals as recorded by sensor 202 and processed in processor 206.

Figure 2:
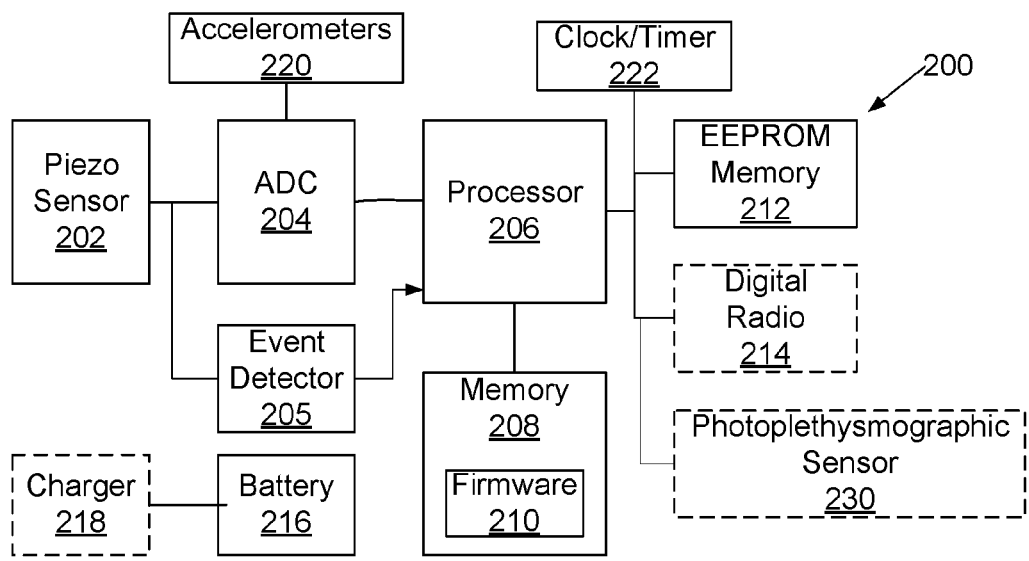
FIG. 2 is a block diagram of an embodiment of the lung function monitor.

Some embodiments of the invention are sensitive to motion artifact, this is overcome by installing the piezoelectric sensor and other components illustrated in FIG. 2 in a mechanically-robust housing prior to mounting the device on the subject's chest.

In embodiments, the firmware 210 executing on processor 206 executes a fast Fourier transform (FFT) upon the digitized audio signals, then uses a gated recurrent unit (GRU) with partial reset (GRUPR) neural network (FIG. 7) to identify wheeze frames in the input signal from ADC 204.

Figure 7:
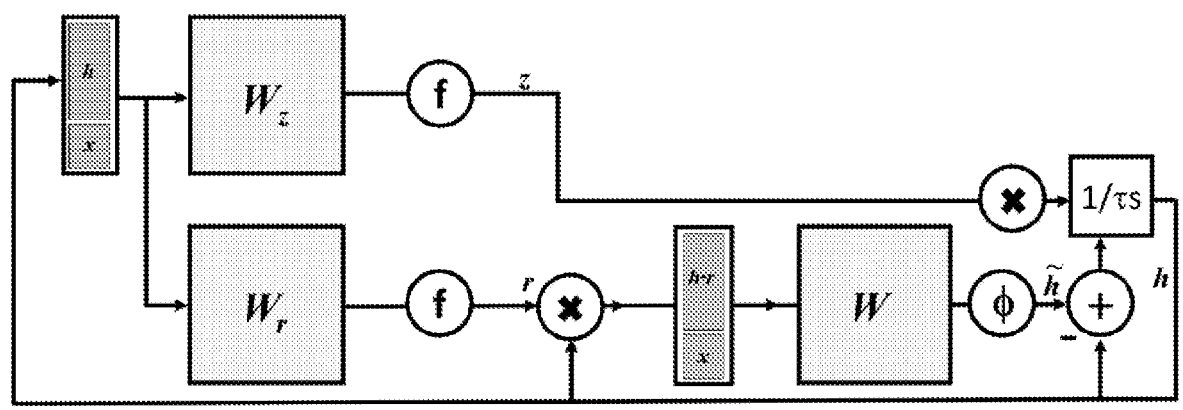
FIG. 7 is a block diagram of a GRU neural network unit.

The firmware then calculates wheeze severity. The variables x, h and h of FIG. 7 are the input, current internal state and candidate new state, respectively. Also, r and z are gating variables. A table inset compares GRU performance to traditional Mel frequency cepstral coefficient (MFCC) plus hidden Markov model (HMM). Wheeze severity is calculated as a ratio of wheeze frames to total number of frames in a breathing cycle. The GRU is robust to PZT non-idealities; we previously showed that it outperforms other algorithms in detecting cough from a PZT signal in a realistic everyday environment with motion artifact.

Our event detector 205, 800 (FIG. 8) is based on a low power, analog parametric model of wheeze. The model estimates "wheeze parameters" of an incoming signal in real time and then uses these parameters to reconstruct a hypothesized wheeze signal. A similarity measure is then calculated between the reconstructed wheeze and the incoming signal: if the two signals are similar, then the incoming signal is likely a wheeze; if the signals are dissimilar, then the wheeze hypothesis failed. The event detection circuit 205 outputs the wake-up flag to processor 206 based on the signals' level of similarity.

For asthmatic wheeze, the parametric model we use is a polyphonic signal, where most of the energy is contained in the fundamental, second and third harmonics. The harmonics' short-time frequencies are the "wheeze parameters" of interest, which we can estimate with a wheeze hypothesis unit (WHU) that comprises a network of coupled adaptive bandpass filters (FIG. 8) with integer-multiple center frequencies. The coupled filter network is described by Equation 1:

$$x''\_1 = -\omega x'\_1 - \omega^2 x\_1 + \omega^2 u; x''\_2 = -2\omega x'\_2 - [4\omega]^2 x\_2 + [4\omega]^2 u; x''\_3 = -3\omega x'\_3 - [9\omega]^2 x\_3 + [9\omega]^2 u$$

$$\omega' = (u - x\_1 - x\_2 + x\_3) x'\_1 / \sqrt{(x\_1^2 + x'\_1^2)} - \omega$$

Here, u is the input signal and x1,2,3 are the outputs of three coupled bandpass filters with harmonically-related center frequencies, as we described in.

Figure 8:
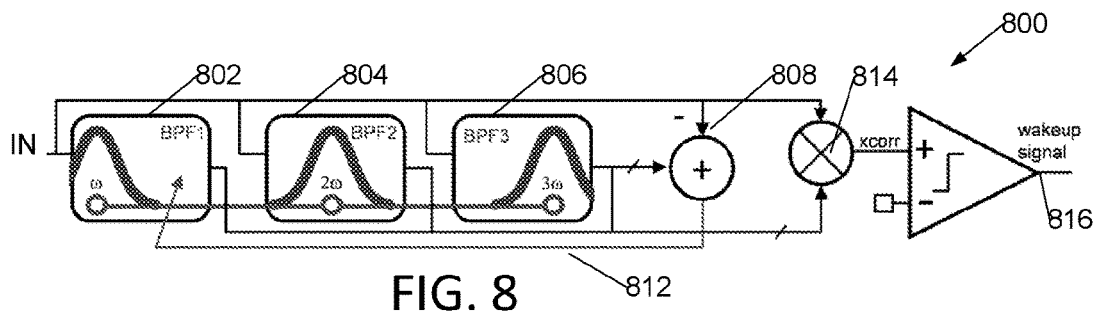
FIG. 8 is a block diagram of the event detector used to generate wakeup signals to the processor.
Figure 9A:
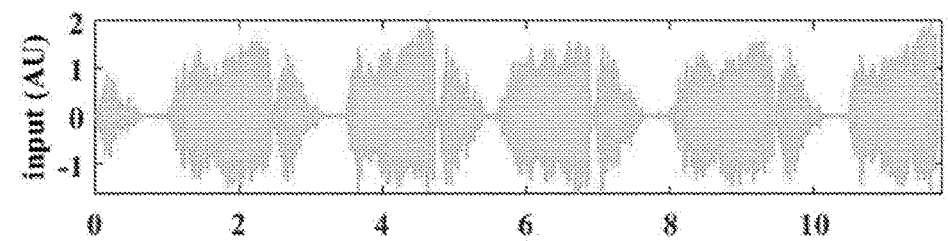
FIG. 9A represent a series of breath sounds, including some sounds with wheezes, in time domain, under low noise conditions.
Figure 9B:
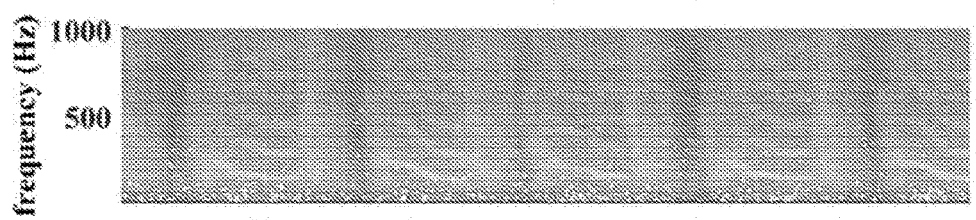
FIG. 9B represents the series of breath sounds of FIG. 9A transformed to frequency domain.
Figure 9C:
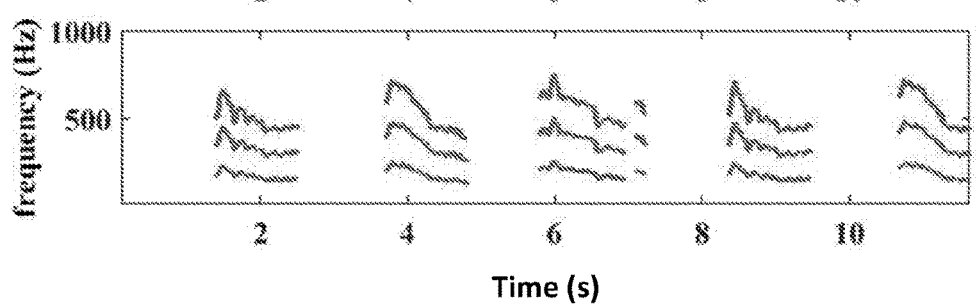
FIG. 9C represents response of three filters to the series of sounds of FIG. 9A.

FIGS. 9A, 9B, 9C, and 10 illustrate the operation of the event detector 205, 800 (FIGS. 2 & 8). First, the incoming signal, as illustrated in FIGS. 9A and 9B is input to the bandpass filters 802, 804, 806. Then, the sum of the filters' outputs at adder 808 is subtracted by subtractor 810 from the incoming signal to generate an error term 812, which is minimized for a particular subject by tuning the filter center frequencies via a feedback loop. If the incoming signal is indeed a wheeze, then the filter center frequencies will eventually track the signal's harmonics, and the reconstructed wheeze signal (i.e. the sum of the filters' outputs) will resemble the original, incoming signal. Cross-correlation 814 is used as a similarity measure between these two signals, and the wake-up signal 816 to the processor 206 is set high if the cross-correlation exceeds 0.6.

Figure 10A:
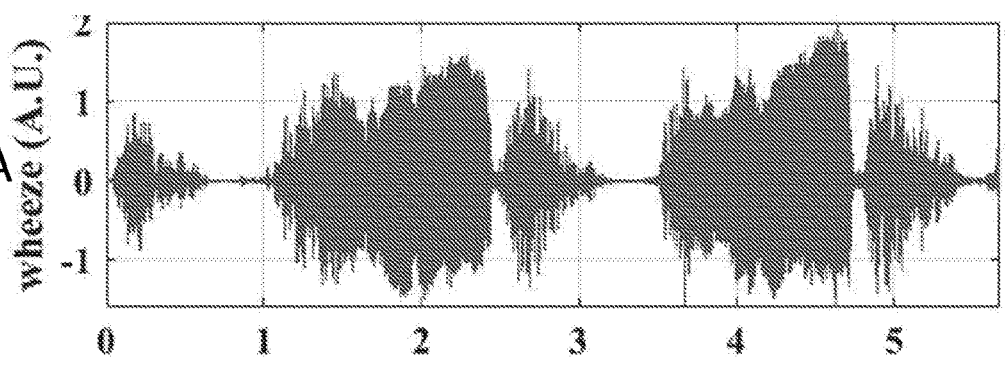
FIGS. 10A-10B represents output of the correlation circuit showing detection of candidate wheeze sounds by the event detector.
Figure 10B:
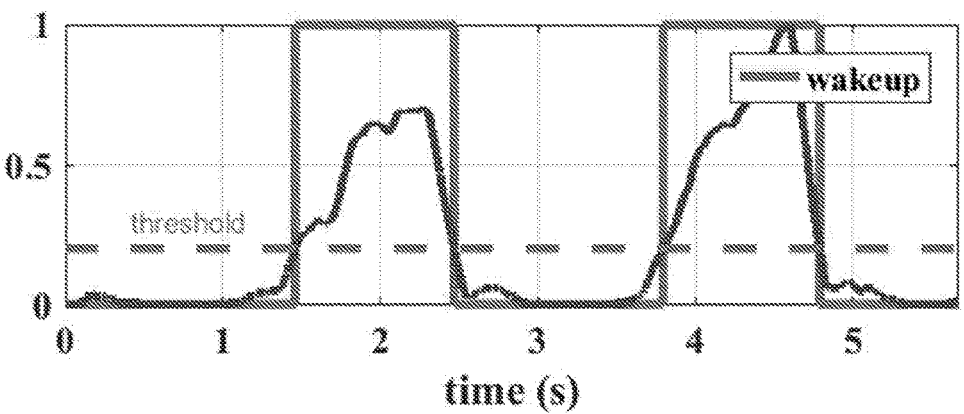

The event detector 205, 800, as described above, performs as illustrated in FIGS. 10A and 10B; FIG. 10A illustrating audio as detected by piezoelectric sensor 202 and FIG. 10B illustrates detected wheeze and wakeup signals.

Figure 11:
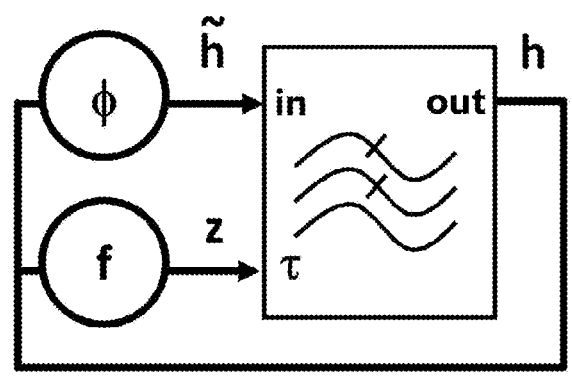
FIG. 11 illustrates a simplified GRU neural network using partial reset (GRUPR) used to classify received audio to confirm detection of wheezes.

In an embodiment, the firmware implements the GRUPR neural network using a simplified network as illustrated in FIG. 11, instead of the full GRU of FIG. 7, to confirm detection of wheezes.

Figure 12:
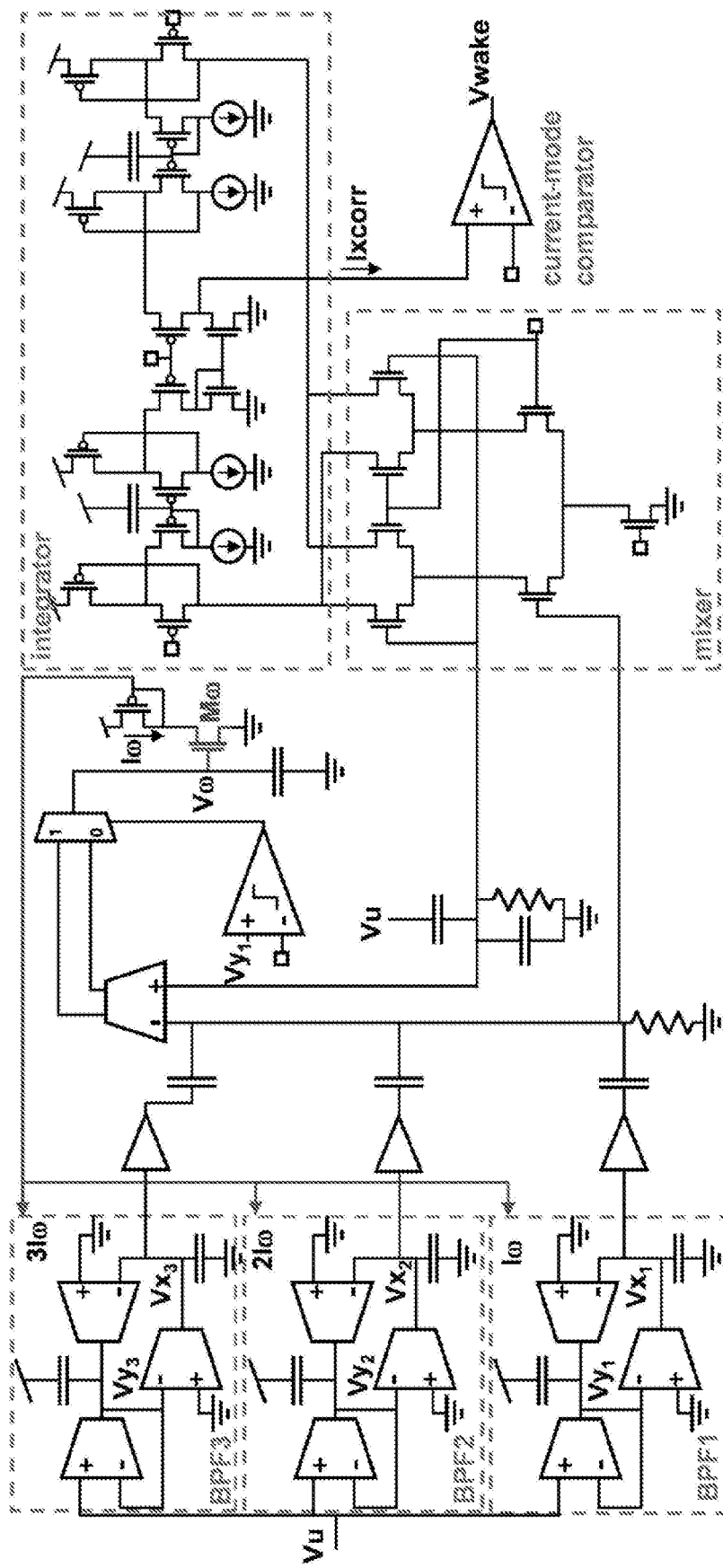
FIG. 12 illustrates a schematic diagram of an application-specific integrated circuit intended to implement the event detector 205, 800 of FIGS. 2 and 8.

In an embodiment the event detector 205 is implemented in an application specific integrated circuit, having a schematic diagram as in FIG. 12.

Weights for the neural networks are determined by optimizing weights, as known in the art of neural networks, for correct detection of wheezes using a training dataset of sounds detected from a chest classified according to wheeze and no wheeze.

Figure 13:
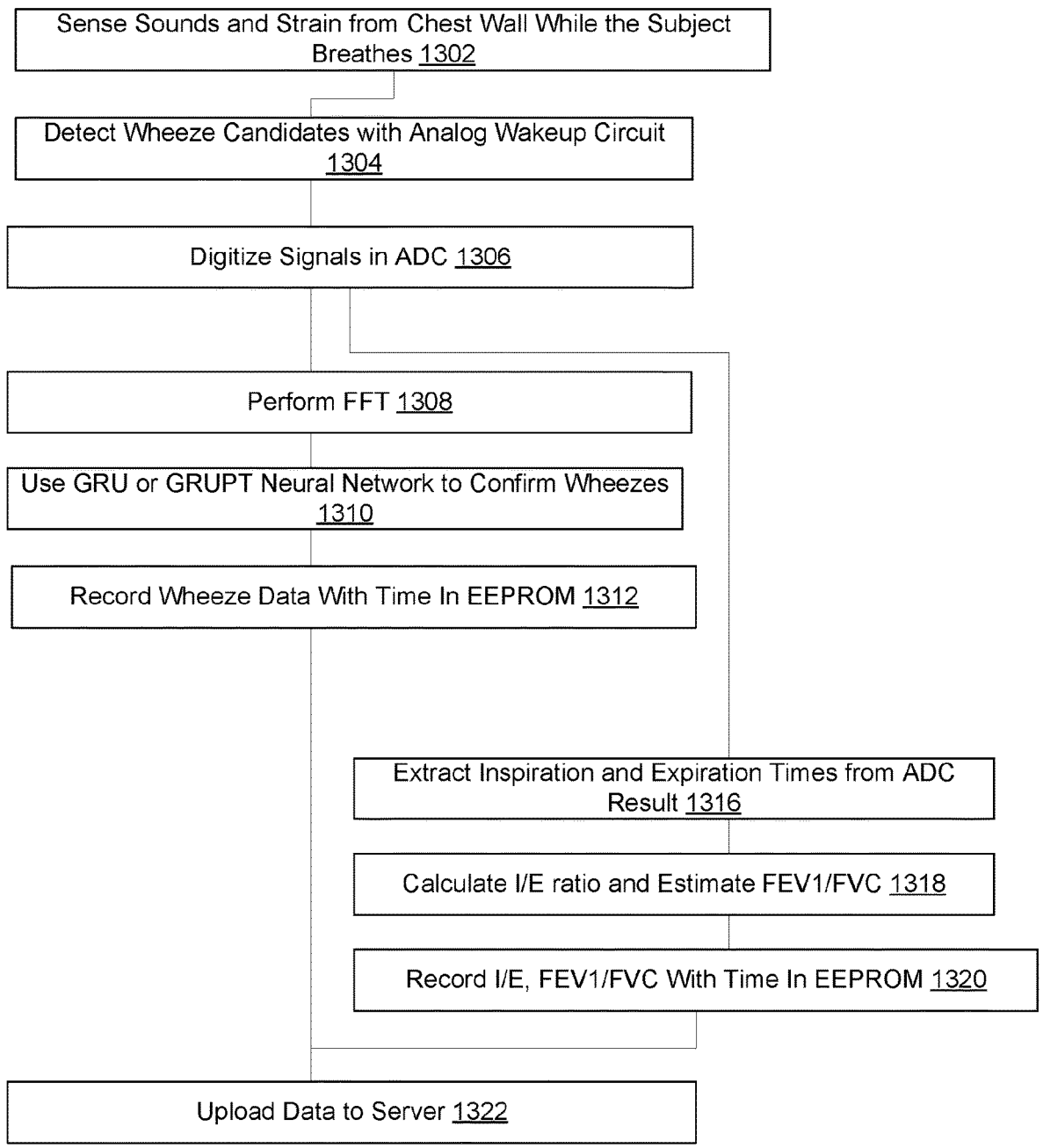
FIG. 13 is a flowchart illustrating operation of an embodiment.

The device operates according to FIG. 13. Sounds are sensed 1302 using the piezoelectric transducer 202, these sounds are provided to the analog wakeup detector 205 where wheeze candidate sounds are detected 1304. When the analog wakeup detector finds candidate wheezes, the processor 206 is awakened and sensed sounds are digitized 1306 in the ADC 204. The processor then performs an FFT 1308 and uses a GRU or GRUPT neural network to confirm 1310 wheezing, wheezing events are recorded 1312 with time of event and severity of wheezing in the EEPROM. In embodiments with a photoplethysmographic sensor 230, oxygen saturation is recorded with each wheezing event time and severity. In alternative embodiments, coughing events are also detected and recorded in the EEPROM with time and severity of coughing, and if photoplethysmographic sensor 230 is present, oxygen saturation. When the processor 206 is awakened, the processor also extracts 1316 inspiration and expiration times from the digitized sound and strain information, then calculates 1318 an inspiration/expiration (I:E) ratio from those times and estimates FEV1:FVC ratios from them. The I:E ratio and/or FEV1:FVC ratio are also recorded 1320 with time of measurement for each wheezing event in the EEPROM; clock-timer 222 may also awaken the processor 206 to record additional I:E ratios and/or FEV1:FVC, and blood oxygen saturation in embodiments with a photoplethysmographic sensor 230, in the EEPROM at preprogrammed times.

Data from the EEPROM for each wheezing or coughing event, and data recorded at preprogrammed times, is uploaded 1322 to a server over the internet either by manual removal of an EEPROM, in form of an SD card, and use of a workstation; or by short-range digital radio through a body area network hub or cell phone and internet to the server. Once on the server, data is processed and made available to a physician.

To our knowledge, no device presently on the market can passively estimate a patient's FEV/FVC, all other devices require effort and cooperation of the patient. The current gold standard for lung function testing is an in-hospital spirometry test, administered in the pulmonary function testing laboratory. This is an expensive test that requires (1) effort from the patient (2) correct breathing maneuver technique from the patient (3) trained staff to administer the test. Home spirometry tests are less expensive than the in-hospital tests, but they still require (1) effort from the patient (2) correct breathing maneuver technique from the patient.

Our PULMO device requires no effort or specialized technique from the patient. It is therefore amenable to high patient adherence, and is appropriate for use in children.

Asthma is the most common pediatric chronic condition in the US. It affects six million children, causes 0.8 million pediatric emergency department visits and accounts for $18 billion a year in healthcare costs. The invention would enable fewer, more efficient office visits and fewer in-hospital pulmonary function tests (PFTs) than otherwise needed to achieve asthma control. Moreover, compared to other asthma tools, the proposed device's physical unobtrusiveness and minimal interaction requirements will promote its acceptability and adherence to use. In aggregate, the inventive device will advantageously have immediate and significant impact in reducing the time and healthcare resources needed to establish control of asthma in newly-diagnosed children.

Combinations

The features and methods described herein may appear in devices in various combinations. Among those combinations are:

A device designated A for automatically detecting and quantifying lung function includes a piezoelectric sensor configured for attachment to a chest wall, with an analog to digital converter coupled to receive signals from the piezoelectric sensor and provide digitized signals to a processor. The processor operates under control of firmware in memory to detect wheezing sounds in the digitized signals. Sounds are also provided from the piezoelectric sensor to an analog event detector configured to wake-up the processor upon detection of candidate wheeze sounds.

A device designated AA including the device designated A wherein the processor is configured to determine inspiration duration and expiration duration from the digitized signals, and to compute an inspiration expiration ratio therefrom.

A device designated AB including the device designated A or AA wherein the analog event detector comprises a plurality of bandpass filters coupled to a modeling circuit, the modeling circuit coupled to a correlation circuit.

A device designated AC including the device designated AB wherein the bandpass filters of the analog event detector have bandpass automatically adjusted by feedback from a circuit within the analog event detector.

A device designated AD including the device designated A, AA, AB, or AC wherein the processor detects wheezing sounds in the digitized signals by performing a fast Fourier transform (FFT) to transform the digitized signals to frequency domain, followed by performing a neural network method to detect wheezes.

A device designated AE including the device designated AD wherein the neural network method uses a gated recurrent unit (GRU) with partial reset (GRUPR) neural network to detect wheezes.

A device designated AF including the device designated A, AA, AB, AC, AD, or AE further comprising a photoplethysmographic sensor coupled to the processor, the photoplethysmographic sensor adapted to measure blood oxygen saturation.

A device designated AG including the device designated A, AA, AB, AC, AD, AE, or AF further comprising a memory adapted to store data comprising time and severity of detected wheezing events.

A device designated AH including the device designated AG further comprising a digital radio, and wherein the processor is configured by firmware to upload the data comprising time and severity of wheezing events through the digital radio.

A method designated B of determining lung function includes sensing sounds using a piezoelectric transducer; providing sounds to an analog wakeup detector; when wheeze candidate sounds are detected, waking a processor; converting sounds to digital sounds; performing a fast Fourier transform on digital sounds; using a neural network to confirm wheezing; and recording wheezing events.

A method designated BA including the method designated B and further includes: extracting inspiration and expiration times from the digitized sounds; and calculating an inspiration/expiration (I:E) ratio from the inspiration and expiration times.

A method designated BB including the method designated B or BA and further including uploading I:E ratio and wheeze data to a server.

Changes may be made in the above system, methods or device without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A device for automatically detecting and quantifying lung function comprising:
   a piezoelectric sensor configured for attachment to a mammalian chest wall;
   an analog to digital converter coupled to receive analog signals generated by the piezoelectric sensor and provide digitized signals to a processor;
   the processor operating under control of firmware in memory to confirm breathing-related event-of-interest sounds are represented in the digitized signals;
   an analog event detector coupled to receive the analog signals from the piezoelectric sensor, configured to detect breathing-related event-of-interest candidate sounds in the analog signals, and coupled to wake-up the processor only upon the detection of the breathing-related event-of-interest candidate sounds in the analog signals to confirm the breathing-related event-of-interest sounds in the digitized signals upon the detection of the breathing-related event-of-interest candidate sounds in the analog signals, the analog event detector comprising a plurality of bandpass filters each coupled to receive the analog signals from the piezoelectric sensor.

2. The device of claim 1 wherein the processor is configured to determine inspiration duration and expiration duration from the digitized signals, and to compute an inspiration-expiration ratio therefrom.

3. The device of claim 1 wherein the plurality of bandpass filters of the analog event detector are coupled to a modeling circuit, the modeling circuit coupled to a correlation circuit.

4. The device of claim 3 wherein the bandpass filters of the analog event detector have bandpass automatically adjusted by feedback from a circuit within the analog event detector.

5. The device of claim 1 wherein the processor confirms the breathing-related event-of-interest sounds in the digitized signals using a fast Fourier transform (FFT) to transform the digitized signals to frequency domain, followed by a neural network method to detect the breathing-related event-of-interest.

6. The device of claim 5 wherein the neural network method is a gated recurrent unit (GRU) with partial reset (GRUPR) neural network method.

7. The device of claim 1 further comprising a photoplethysmographic sensor coupled to the processor, the photoplethysmographic sensor adapted to measure blood oxygen saturation.

8. The device of claim 3 further comprising a memory adapted to store data comprising time and severity of detected breathing-related event-of-interest events.

9. The device of claim 1, further comprising a memory adapted to store data comprising time and severity of detected breathing-related event-of-interest events.

10. The device of claim 1 further comprising a digital radio, and wherein the processor is configured by firmware to upload data comprising time and severity of breathing-related event-of-interest events through the digital radio.

11. The device of claim 5 wherein the processor is further configured by firmware to estimate at least one lung function parameter selected from the group consisting of forced expiratory volume in one second (FEV1), forced vital capacity (FVC) and a FEV1/FVC ratio from the digitized signals.

12. The device of claim 1, wherein the breathing-related event-of-interest sounds correspond to a breathing-related event-of-interest is-selected from a group of events-of-interest consisting of wheezing events, coughing events, and inhaler use.

13. A method of determining lung function comprising:
   sensing sounds using a piezoelectric transducer;
   providing sounds to an analog candidate detector, the analog candidate detector comprising a plurality of analog bandpass filters coupled to receive analog signals from the piezoelectric transducer representing the sounds;
   using the analog candidate detector, determine a similarity measure between the analog signals and an analog parametric model of breathing-related event-of-interest candidate sounds, and output a wake-up flag in response to the similarity measure being above a threshold; and
   in response to the wake-up flag:
     waking a processor;
     converting the analog signals representing the sounds to digital signals representing the sounds;
     performing a fast Fourier transform on the digital signals using the processor;
     using a neural network in the processor to confirm breathing-related event-of-interest represented in the digital signals as one or more specific breathing-related event-of-interest events;
     and recording breathing-related event-of-interest events.

14. The method of claim 13 further comprising:
   extracting inspiration and expiration times from the digitized sounds; and calculating an inspiration/expiration (I:E) ratio from the inspiration and expiration times.

15. The method of claim 14 further comprising uploading the I:E ratio and the recorded one or more breathing-related event-of-interest events to a server.

16. The method of claim 13, wherein the breathing-related event-of-interest is selected from a group of events-of-interest consisting of wheezing events, coughing events, and inhaler use.

17. A device for automatically detecting and quantifying lung function comprising:
   a contact microphone configured for attachment to a mammalian chest wall; and
   an analog event detector configured to receive analog signals from the contact microphone and generate a wake-up flag when the analog signals are sufficiently similar to an analog parametric model of breathing-related event-of-interest candidate sounds;
   an analog to digital converter coupled to digitize signals from the contact microphone in response to the wake-up flag, and provide the digitized signals to a processor;
   wherein the processor is configured by firmware in memory to determine inspiration duration and expiration duration from the digitized signals, and to compute an inspiration-expiration ratio therefrom; and wherein the processor is further configured by firmware to estimate at least one lung function parameter selected from the group consisting of forced expiratory volume in one second (FEV1), forced vital capacity (FVC) and a FEV1/FVC ratio from the digitized signals.

18. The device of claim 17 wherein the processor is further configured by firmware to estimate a FEV1/FVC ratio.

19. The device of claim 17 wherein the processor is further configured by firmware in memory to detect breathing-related event-of-interest sounds in the digitized signals.

20. The device of claim 19, wherein the breathing-related event-of-interest sounds correspond to a breathing-related event-of-interest is-selected from a group of events-of-interest consisting of wheezing events, coughing events, and inhaler use.

* * * * *